(12) United States Patent
Epple et al.

(10) Patent No.: US 11,123,538 B2
(45) Date of Patent: Sep. 21, 2021

(54) CATHETER PUMP WITH DRIVE UNIT AND CATHETER

(71) Applicant: CardioBridge GmbH, Hechingen (DE)

(72) Inventors: Klaus Epple, Rangendingen (DE); Andreas Fritz, Moessingen (DE)

(73) Assignee: CardioBridge GmbH, Hechingen (DE)

(*) Notice: Subject to any disclaimer, the term of this patent is extended or adjusted under 35 U.S.C. 154(b) by 306 days.

(21) Appl. No.: 16/484,809

(22) PCT Filed: Feb. 8, 2018

(86) PCT No.: PCT/EP2018/053130
§ 371 (c)(1),
(2) Date: Aug. 8, 2019

(87) PCT Pub. No.: WO2018/146176
PCT Pub. Date: Aug. 16, 2018

(65) Prior Publication Data
US 2020/0023113 A1 Jan. 23, 2020

(30) Foreign Application Priority Data
Feb. 13, 2017 (DE) .................... 10 2017 102 825.0

(51) Int. Cl.
A61M 60/205 (2021.01)
A61M 60/135 (2021.01)
(Continued)

(52) U.S. Cl.
CPC ........ A61M 60/135 (2021.01); A61M 60/205 (2021.01); A61M 60/414 (2021.01); A61M 60/419 (2021.01); A61M 25/0082 (2013.01)

(58) Field of Classification Search
CPC ............ A61M 25/0082; A61M 60/135; A61M 60/205; A61M 60/414; A61M 60/419
See application file for complete search history.

(56) References Cited

U.S. PATENT DOCUMENTS

2011/0238172 A1 9/2011 Akdis
2012/0059460 A1* 3/2012 Reitan ................. A61M 1/1024
623/3.12
2015/0290371 A1 10/2015 Muller et al.

FOREIGN PATENT DOCUMENTS

DE 10 2006 036 948 A1 2/2008
EP 2 288 392 B1 11/2013
(Continued)

Primary Examiner — George Manuel
(74) Attorney, Agent, or Firm — Aslan Law, P.C.

(57) ABSTRACT

A catheter pump having a drive unit and a catheter. The catheter has a pump head for inserting into the aorta and having a rotatably arranged rotor shall for driving an expandable conveying element provided on the pump head and has, at the proximal end thereof, a coupling section, which is connected to the rotor shaft for conjoint rotation and which can be rotated about a coupling axis. The drive unit having a drive and a drive section, which can be driven in rotation about a drive axis by the drive, the coupling section and/or the drive section having magnet elements for contactless mutual rotational coupling. The coupling and drive axes being spaced from each other by a distance a in the perpendicular direction in such a way that the magnetic field of the magnet elements pushes the coupling section in a direction extending perpendicularly to the coupling axis.

20 Claims, 3 Drawing Sheets

(51) Int. Cl.
*A61M 60/414* (2021.01)
*A61M 60/419* (2021.01)
*A61M 25/00* (2006.01)

(56) References Cited

FOREIGN PATENT DOCUMENTS

| | | |
|---|---|---|
| JP | 2011525385 A | 9/2011 |
| JP | 2013150693 A | 8/2013 |
| WO | WO 2009/046790 A2 | 4/2009 |
| WO | WO 2010/127871 A1 | 11/2010 |
| WO | WO 2012/127871 A1 | 9/2012 |
| WO | WO 2014/ 140 282 A1 | 9/2014 |
| WO | WO 2016/118781 A2 | 7/2016 |

* cited by examiner

CATHETER PUMP WITH DRIVE UNIT AND CATHETER

CROSS-REFERENCE TO RELATED APPLICATIONS

This application claims priority to German Patent Application No. 10 2017 102 825.0 filed on Feb. 13, 2017, and to PCT Application No. PCT/EP2018/053130 filed on Feb. 8, 2018, the entire contents of which are hereby incorporated by reference.

The invention relates to a catheter pump with a drive unit and a catheter, wherein the catheter has a pump head for insertion into the arterial vascular system such as the aorta or the heart, a rotatably mounted rotor shaft for driving an expandable pumping element provided on the pump head, and at its free end, a coupling section that rotates around a coupling axis and has a rotationally fixed connection to the rotor shaft, and wherein the drive unit has a drive and a drive section that is drivable in a rotary motion around a drive axis.

These types of catheter pump are known from EP 2 288 392 B 1, for example, and shown there in FIG. 1a. As a rotating pumping element, for example, as described in EP 2 288 392 B 1, a rotor with foldout propellers may be used, which is provided at the distal end of the catheter. It is also conceivable that differently shaped pumping elements may be used, such as a spiral fashioned into the shape of a helix.

A catheter pump with features of the preamble of patent claim 1 is known from WO 2010/127871 A1. Further similar pumps are disclosed in WO 2016/118781 A1 and WO 2009/046790 A2. A blood pump with a magnetic coupling is known from DE 10 2006 036 948 A1.

Catheter pumps are inserted into the aorta of patients as a temporary circulatory support system, especially when the natural heart is unable to provide the body with sufficient oxygenated blood. The pumping element and the rotor shaft are operated at comparatively high speeds in the range of 7,000 to 15,000 revolutions per minute, and in particular in the range of 10,000 to 13,000 revolutions. A noise has been found to be problematic, particularly around the coupling of the coupling section and the drive section. Especially at these high speeds, disturbing vibration and whistling noises occur. The pump head of the catheter pump may remain in the aorta for several days, especially after surgery.

Therefore the object of the present invention is to provide a catheter pump as described above that has a reliable coupling of the coupling section with the drive section and can still be operated quietly.

This object is achieved with a catheter pump that has the features of claim 1. This causes the coupling section to be urged in a defined direction due to the magnets and occupy a stable position when within the nominal speed range, i.e. particularly a speed from 8000 to 13000 rpm. As a result, on the one hand, a secure magnetic coupling is ensured, and on the other hand, a very quiet operation of the catheter pump is made possible. It has been found that when the coupling axis has no offset to the drive axis, due to the rotating magnetic field of the magnetic elements, the coupling section does not occupy a defined radial position during rotation and moves between different, undefined positions, which overall leads to disturbing vibrations and noise. It is provided that the distance a is in the range of 0.7 mm to 3.5 mm, preferably in the range of 1 mm to 3 mm, and more preferably in the range of 2 mm. This comparatively small center distance is sufficient to ensure that the catheter pump operates with little noise.

It is also advantageous if the coupling section to the drive section in the axial direction has a distance m, wherein the distance m is in the range of 1 mm to 6 mm, preferably in the range of 3 mm to 5 mm, and more preferably in the range of 3.5 mm. Such a distance m, in particular, allows for a fluid-tight arrangement of the coupling section to the drive section to be provided, while sufficient torques may still be transmitted.

Furthermore, it has been found to be advantageous if the rotor shaft has a diameter d, wherein the distance a is in the range of 0.25 to 1.5 times, and preferably in the range of 0.5 to 1.2 times the diameter d. This combination has also resulted in comparatively quiet operation of the catheter pump.

The diameter d may preferably be in the range of 0.7 mm to 4.5 mm, preferably in the range of 1.5 mm to 3 mm, and more preferably in the range of 2 mm. This also results in quiet operation.

In order to ensure a secure coupling of the coupling section with the drive section, it is advantageous if the drive unit has a receptacle for the coupling section, wherein the coupling section occupies an operating position that is offset relative to the drive section in the transverse direction by the distance a. By providing the receptacle, a defined arrangement of the coupling section with respect to the drive section can consequently be ensured.

According to the invention, it may also be provided that the receptacle or a wall bounding the receptacle provides one or more damping elements, which act as vibration dampers against the coupling section. As a result, unwanted residual vibrations of the coupling section can be safely avoided.

In this case, the coupling section may have a magnet holder having magnet elements arranged on it arranged at the free end of the rotor shaft. The magnetic elements may be arranged to extend in a ring around the coupling axis. In addition to the magnetic elements, metal elements or metal rings may also be used for the defined expansion of the magnetic field.

Furthermore, it is advantageous if the coupling section is enclosed by a fluid-tight cap. The cap may be arranged as an extension of an outer catheter enclosing the rotor shaft or a corresponding sleeve, so that the entire pump shaft is arranged fluid-tight inside the catheter and the coupling section is also arranged fluid-tight in the cap.

According to the invention, it is furthermore conceivable that the cap has centering bevels on the side facing the drive section and/or the receptacle on the side facing the coupling section for centering the cap and thus the coupling section in the operating position. In this way, it can be ensured that the cap and thus the coupling section offset by distance a to the drive axis can be inserted into the receptacle.

The catheter may provide an outer catheter and an inner catheter, wherein the rotor shaft is rotatably arranged inside the inner catheter. Furthermore, lubricating and rinsing liquid may be provided, which is supplied to the pump head during operation in order to lubricate and flush the bearings provided there. In particular, the lubricating and rinsing liquid may be guided to the pump head via a lumen provided between the outer catheter and the inner catheter. The recirculated lubricating and flushing liquid may be recirculated via a lumen provided between the rotor shaft and the inner catheter. This may prevent a mixing of the rinsing liquid, which is being transported to the pump head, with the rinsing liquid, which is being recirculated.

The cap may have an outlet and the catheter may be designed such that the lubricating and rinsing liquid, which flows around the rotor shaft during operation, is discharged through the cap and via the outlet from the cap, and thus from the catheter. Such a rinsing of the rotor shaft in the catheter serves, in particular, to lubricate and remove debris, thus allowing the rotor shaft to rotate smoothly in the catheter.

In order to prevent contaminants from reaching the drive section, it is advantageous if the drive unit has a fluid-tight wall section between the receptacle and the drive section. According to this embodiment, the wall section and the cap may both be provided between the coupling section and the drive section. However, due to the still small distance between the drive section and coupling section and the appropriate selection of the magnets, a secure rotational coupling of the drive section to the coupling section can be ensured.

Furthermore, it can be provided that the magnetic elements on the coupling section and/or on the drive section for rotational coupling are designed such that the magnetic coupling tears off at a limit torque. As a result, an overload protection may be provided.

Further embodiments and advantageous embodiments of the invention will become apparent from the following description, with reference to which an embodiment of the invention will be described and explained in more detail.

Figure 1:
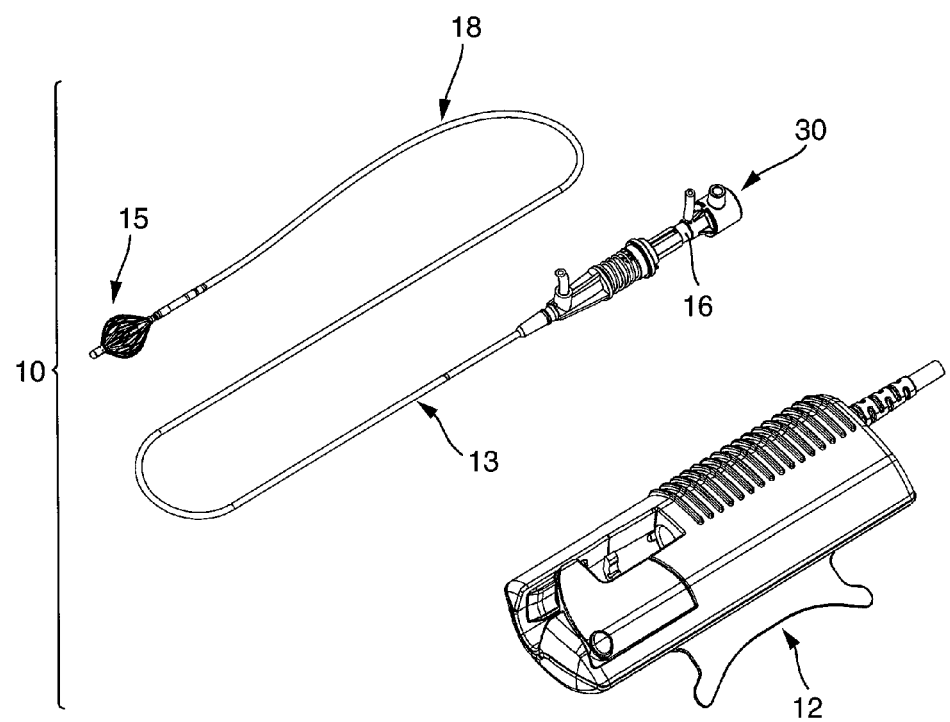
FIG. 1 shows a catheter pump with a drive unit and a catheter.

FIG. 1 shows a catheter pump 10 with a drive unit 12 and a catheter 18 that is couplable to the drive unit 12. The catheter 18 has at its distal end a pump head 15 for inserting into the arterial vasculature, such as the aorta or the heart. In the catheter 18, a rotor shaft 32 is provided, by means of which a pumping element provided in the pump head 15, such as a rotor with foldable propellers, is adapted to be set in rotation. At its proximal end 16, the catheter 18 provides a coupling section 30, which is insertable into the drive unit 12, by means of which ultimately the rotor shaft 32, and thus the pumping element, is operable to be set in rotation.

Figure 2:
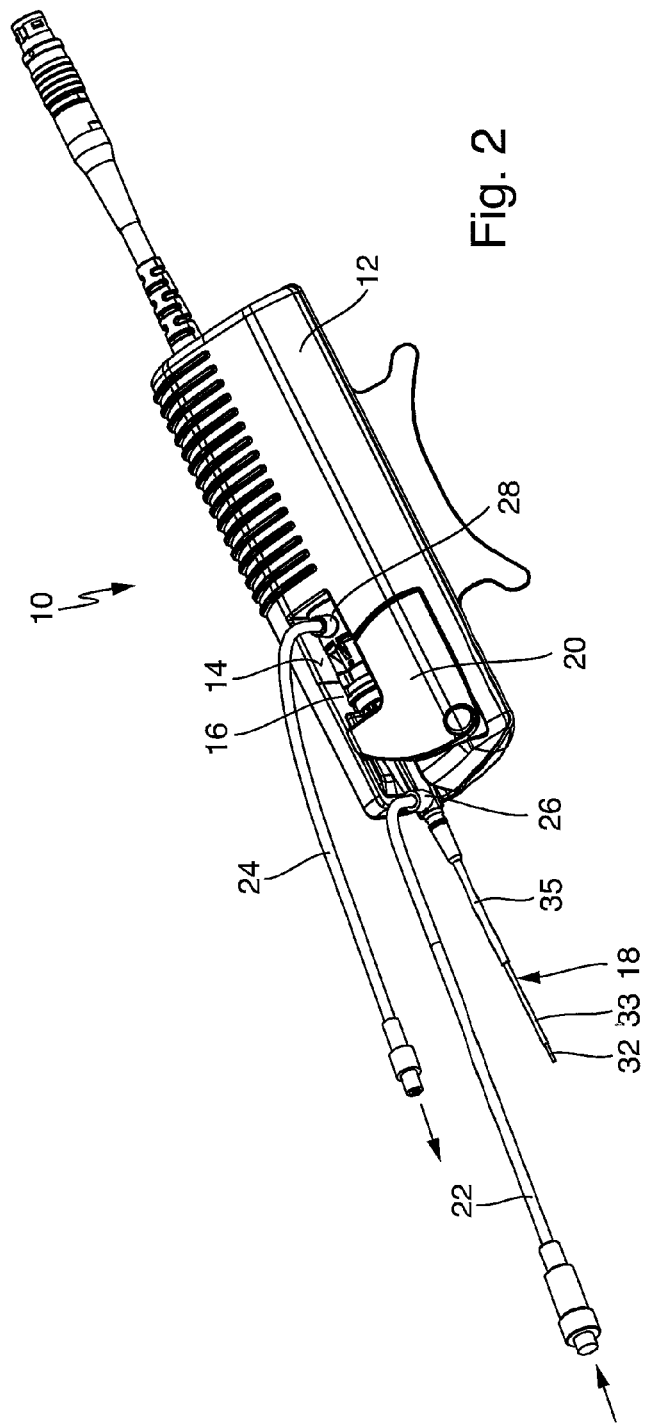
FIG. 2 shows a drive unit of a catheter pump according to the invention in the operating position and FIG. 3 shows an enlarged detail of a longitudinal section through the coupling section and drive section of the drive unit according to FIG. 2.

FIG. 2 shows a drive unit 12 of a catheter pump 10 according to the invention. The drive unit 12 has a receptacle 14. Furthermore, the proximal end 16 of a catheter 18 is shown, which has at its distal end (not shown) the pumping element that rotates during operation.

The proximal end 16 of the catheter 18 is arranged in the receptacle 14 and is securely held there by means of a holding element 20.

At the proximal end 16, two tubes 22, 24 are provided. Flushing and lubricating fluid may be introduced into the catheter 18 through the hose 22 via an inlet 26. This rinsing and lubricating fluid is fed through the catheter 18 to the pump head 15. In the pump head 15, a portion of this lubricating and rinsing fluid is returned again through the catheter 18 and discharged through an outlet 28 and the hose 24. The recirculated lubricating and rinsing liquid is thereby returned between the rotor shaft 32 rotating during operation and an inner catheter 33. The inner catheter 33 is enclosed by an outer catheter 35, whereby lubricating and rinsing fluid is conveyed via the lumen between the inner catheter 33 and the outer catheter 35 towards the pump head 15.

Figure 3:
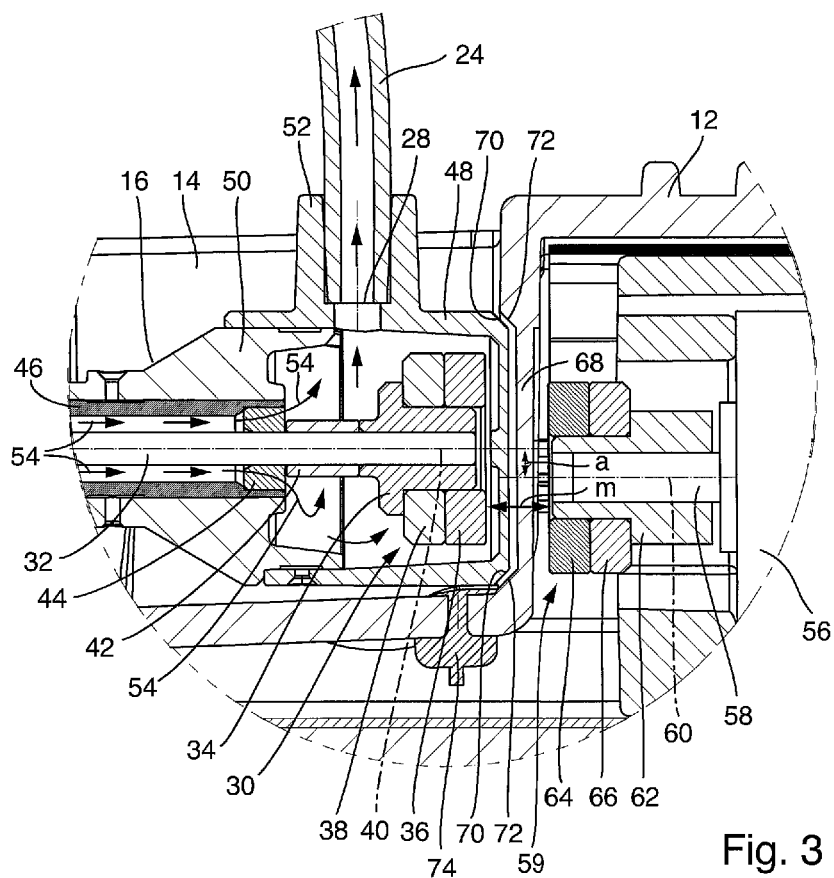

In the detail shown in FIG. 3, the proximal end 16 with the outlet 28 in the receptacle 14 is shown.

It can clearly be seen that the proximal end 16 of the catheter 18 has a coupling section 30, which is rotationally fixed connected to the rotor shaft 32. For this purpose, the coupling section 30 provides a magnet holder 34 on which both a magnetic ring 36 with magnetic elements and a soft iron ring 38 for influencing the magnetic field are arranged. During operation, the coupling section 30 or the magnetic ring 36 is rotatable about the coupling axis 40, which is located in the rotor shaft axis. As such, the rotor shaft 32 is rotatably supported by a shaft 42 and by a bearing 44 in a bearing sleeve 46 at the proximal end 16 of the catheter 18.

As is also clear from FIG. 3, a cap 48 enclosing the coupling section 30 is provided at the free end of the catheter, which cap is arranged in a fluid-tight manner on a sleeve housing 50 accommodating the sleeve 46. The cap 48 provides the outlet 28 and a receiving nozzle 52 for the tube 24. Overall, during operation of the catheter pump 10, the lubricating and rinsing liquid is able to flow between the bearing sleeve 46 and the rotating rotor shaft 32 in the axial direction, as indicated by the arrows 54, through the bearing 44 toward the coupling portion 32 and drain out through the outlet 28 into the tube 24.

As is likewise clear in FIG. 3, a drive 56 in the form of an electric motor is provided in the drive unit 12. The drive 56 may comprise a suitable transmission unit. The drive 56 drives a drive section 59, which provides a driving shaft 58, which is drivable about a drive axis 60 and a magnet holder 62 on which a magnet ring 64 and a soft iron ring 66 are arranged.

The magnetic rings 36 and 64 are formed complementary to each other such that in a rotational turning of the drive section 59, the coupling section 30 is offset for mutual rotational coupling when it turns. The diameter of the magnet ring 64 preferably corresponds to the diameter of the magnet ring 36.

As is also clear from FIG. 3, the coupling axis 40 and the drive axis 60 are spaced apart from each other by a distance a in the transverse direction or offset relative to one another. The distance a is chosen such that the magnetic field generated in the ring magnets 36 and 64 provides a force that urges the coupling section 36 in a direction transverse to the coupling axis 40. By providing the force transverse to the coupling axis, operation of the catheter pump with relatively little noise even when the rotor shaft is running at higher speeds, may be provided.

The axial distance m of the magnetic rings 36 and 64 to each other is preferably in the range of 3 mm to 4 mm. The distance a of the two axes 40 and 60 is preferably in the range of 1.5 mm to 2.5 mm. The distance a is slightly smaller than the diameter of the rotor shaft 32. However, the distances a and m may also vary according to the invention and are dependent on the magnetic force, the design and the number of magnetic elements or the torque to be transmitted.

In order to prevent liquid or media from penetrating into the drive section 59 or the drive 56, a fluid-tight wall 68 is provided between the receptacle 14 and the drive section 59.

In order to ensure a positionally accurate insertion of the proximal end 16 of the catheter 18 into the receptacle 14, the cap 48 on the sides facing the drive section 59 has centering bevels 70, which correspond with the centering bevels 72 provided on the wall 68.

In order to dampen possible residual vibrations, or to take away their resonating body, the receptacle 14 and a wall 14 limiting the receptacle have one or more damping elements 74 which act against the coupling section 30 and its cap 48.

The magnetic elements of the magnet rings 36 and 64 are designed such that a rotational coupling through the wall section 68 and the wall section facing the section of the cap 48 is possible.

When designing the rotary coupling, the property of decoupling may be utilized with a torque that is too high or a speed that is too high. As the load increases, the two corresponding magnetic rings 36 and 64 rotate more and more against each other, wherein above a limit torque or when a limit speed is exceeded, the angle of rotation is too large, and thus decoupling occurs. This property may be used as overload protection.

The invention claimed is:

1. A Catheter pump having a drive unit and a catheter, wherein the catheter comprising:
    a pump head for inserting into the arterial vascular system,
    a rotatably arranged rotor shaft for driving an expandable pumping element provided at a pump head,
    a coupling section operable to rotate around a coupling axis rotationally fixed connected to the rotor shaft,
    the coupling section is located at the proximal end of said catheter,
    the drive unit has a drive and a drive section operable to be rotationally driven around a drive axis by the drive,
    the coupling section and/or the drive section have magnetic elements for contactless mutual rotational engagement,
    the coupling axis and the drive axis are spaced apart from each other in the transverse direction by a distance a which is in the range of 0.7 mm to 6.5 mm, such that the magnetic field of the magnetic elements urges the coupling section in a direction extending transverse to the coupling axis.

2. The Catheter pump according to claim 1, wherein the distance a is in the range of 1 mm to 3 mm.

3. The Catheter pump according to claim 1, wherein the coupling section has a distance m to the drive section in the axial direction, and,
the distance m is in the range of 2 mm to 6 mm.

4. The Catheter pump according to claim 1, wherein the rotor shaft has a diameter d, wherein the distance a is in the range of 0.5 to 1.5 times, the diameter d.

5. The Catheter pump according to claim 4, wherein the diameter d is in the range of 0.7 mm to 4.5 mm.

6. The Catheter pump according to claim 4, wherein the diameter d is in the range of 1.5 ram to 3 mm.

7. The Catheter pump according to claim 4, wherein the diameter d is in the range of 2 mm.

8. The Catheter pump according to claim 1, wherein the drive unit has a receptacle for the coupling section wherein the coupling section in the receptacle occupies an operating position offset relative to the drive section in the transverse direction by the distance a.

9. The Catheter pump according to claim 8, wherein the receptacle or a wall limiting the receptacle provides one or more damping elements which act against the coupling section for vibration damping.

10. The Catheter pump according to claim 1, wherein the coupling section has a magnet holder arranged at the free end of the rotor shaft and having magnetic elements arranged thereon.

11. The Catheter pump according to claim 1, wherein the coupling section is enclosed by a fluid-tight cap.

12. The Catheter pump according to claim 11, wherein the cap on the side facing the drive section and/or the receptacle on the side facing the coupling section has centering bevels for centering the cap in the operating position.

13. The Catheter pump according to claim 12, wherein the cap has an outlet and that the catheter is designed such that the rotor shaft is flushed during operation by a rinsing liquid, and
the rinsing liquid is discharged via the outlet.

14. The Catheter pump according to claim 11, wherein the cap has an outlet and that the catheter is designed such that the rotor shaft is flushed during operation by a rinsing liquid, and
the rinsing liquid is discharged via the outlet.

15. The Catheter pump according to claim 1, wherein the drive unit has a fluid-tight wall section between the receptacle and the drive section.

16. The Catheter pump according to claim 1, wherein the magnetic elements on the coupling section and/or on the drive section are designed for rotational coupling such that at a limit torque, the magnetic coupling tears off.

17. The Catheter pump according to claim 1, wherein the distance a is in the range of 2 mm.

18. The Catheter pump according to claim 1, wherein the coupling section has a distance m to the drive section in the axial direction, and
the distance m is in the range of 3 mm to 5 mm.

19. The Catheter pump according to claim 1, wherein the coupling section has a distance in to the drive section in the axial direction, and
the distance m is in the range of 3.5 mm.

20. The Catheter pump according to claim 1, wherein the rotor shaft has a diameter d, wherein the distance a is in the range of 0.8 to 1.2 times, the diameter d.

* * * * *